United States Patent [19]
Vallana et al.

[11] Patent Number: 5,762,870
[45] Date of Patent: Jun. 9, 1998

[54] EXCHANGE STRUCTURE FOR BIOMEDICAL EQUIPMENT

[75] Inventors: Franco Vallana, Turin; Stefano Rinaldi, Parma; Giampiero Porro, Como; Massimo Fini, Mirandola, all of Italy

[73] Assignee: Sorin Biomedica Cardio S.p.A., Saluggia, Italy

[21] Appl. No.: 831,960

[22] Filed: Apr. 2, 1997

Related U.S. Application Data

[63] Continuation of Ser. No. 434,008, May 3, 1995, abandoned.

[30] Foreign Application Priority Data

May 6, 1994 [IT] Italy .................. TO94A0368

[51] Int. Cl.$^6$ ......................................... A61M 1/20
[52] U.S. Cl. .............. 422/48; 210/321.78; 210/321.87; 210/247; 210/456; 210/636
[58] Field of Search ............ 422/48; 261/DIG. 28; 210/321.69, 321.78, 321.81, 321.87, 321.88, 321.89, 247, 456, 636

[56] References Cited

U.S. PATENT DOCUMENTS

| | | | |
|---|---|---|---|
| 3,070,092 | 12/1962 | Wild et al. | |
| 3,386,583 | 6/1968 | Merten | 210/321.86 X |
| 3,893,926 | 7/1975 | Awad | 210/321.79 X |
| 3,915,650 | 10/1975 | Talonn et al. | |
| 4,346,006 | 8/1982 | Kopp et al. | 422/48 X |
| 4,351,797 | 9/1982 | Bellhouse et al. | 422/48 |
| 4,428,934 | 1/1984 | Raible | |
| 4,698,207 | 10/1987 | Bringham et al. | |
| 4,846,977 | 7/1989 | DeVellis | 210/640 |
| 5,100,549 | 3/1992 | Langerak et al. | 210/321.8 |
| 5,169,529 | 12/1992 | Carroll et al. | 210/321.78 |
| 5,244,930 | 9/1993 | Trudell et al. | |

FOREIGN PATENT DOCUMENTS

| | | |
|---|---|---|
| 0080777 | 6/1983 | European Pat. Off. |
| 0251729 | 1/1988 | European Pat. Off. |
| 0341979 | 11/1989 | European Pat. Off. |
| 0292445 | 9/1990 | European Pat. Off. |
| 0521430 | 1/1993 | European Pat. Off. |
| 2404439 | 9/1978 | France |

*Primary Examiner*—Timothy McMahon
*Attorney, Agent, or Firm*—Popovich & Wiles, P.A.

[57] ABSTRACT

The structure has a core which may be a strand or braid, as well as a sheath surrounding the core and defining the exchange surface. Preferred applications are for biomedical equipment such as blood oxygenators and blood purification equipment.

15 Claims, 2 Drawing Sheets

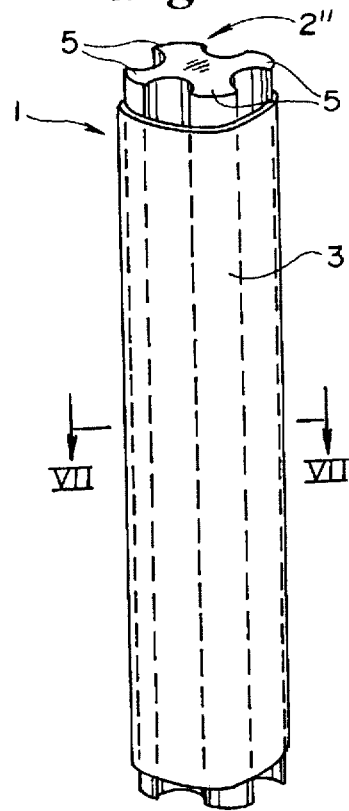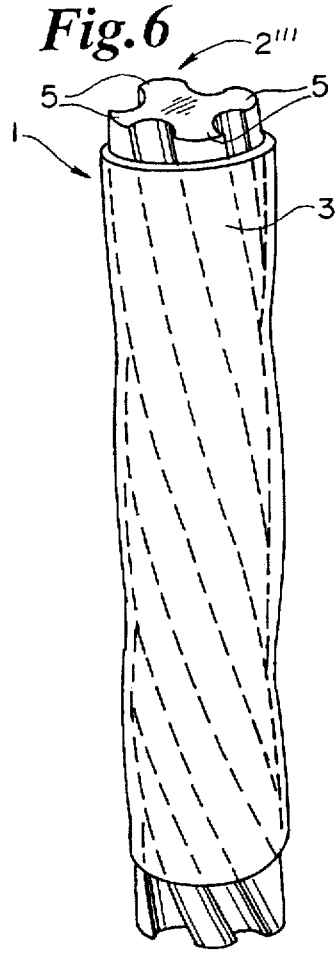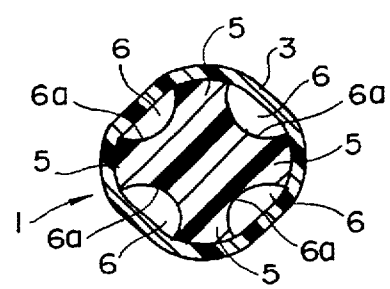

EXCHANGE STRUCTURE FOR BIOMEDICAL EQUIPMENT

This is a continuation of application Ser. No. 08/434,008 filed May 3, 1995 now abandoned.

FIELD OF THE INVENTION

The invention relates to exchange structures. The invention has been developed with particular concern for its possible use, for example, in the field of biomedical equipment.

In this context not only are mass-exchange structures currently utilized (such as those present in devices for the oxygenation of blood or for the purification of blood), but also heat-exchange structures (for example for the production of heat exchangers usable together with blood oxygenators). Substantially similar structures can be utilized in industrial fields for various purposes, for example, for purification processes based on a reverse osmosis mechanism A characteristic common to almost all these structures is that they provide for the arrangement, or flow, of at least two media (usually fluids) in at least locally facing positions so as to cause an exchange, usually of mass and/or heat, between these two media by various mechanisms.

DESCRIPTION OF THE PRIOR ART

For mass transfer or exchange structures, such as blood oxygenators, (it should however be specified that the invention is not intended to be limited in any way to this specific context or application), at least four different types of configurations have been proposed and utilized in the art:

bubble oxygenators (see for example U.S. Pat. No. 3,915,650 and U.S. Pat. No. 4,428,934);

film oxygenators (see for example U.S. Pat. No. 3,070,092 and the description contained in the introductory part of U.S. Pat. No. 5,244,930);

flat membrane oxygenators (see for example U.S. Pat. No. 4,698,207); and hollow fiber oxygenators (see for example EP-A-O 292 445).

Film or bubble oxygenators have numerous elements which are critical in their operation, such as, for example, the problem of eliminating the bubbles of residual gas in the oxygenated blood before it is reintroduced into the patient's blood.

Membrane oxygenators pose production problems, above all as regards the orientation of the membrane, which must be preserved as far as possible during use; this requirement imposes the need for extremely complex mechanical support structures.

Hollow fiber oxygenators resolve many of the problems inherent in the other structures. They have, however, the disadvantage of becoming subject, during use, to phenomena of accumulation and condensation of water vapor and organic materials (typically proteins) which cause their operating efficiently to deteriorate gradually. This happens especially since the material of the fibers, originally hydrophobic, tends gradually to become hydrophilic. In general, also, so that they can be self-supporting without risk of collapse or rupture as a result of the pressure gradients applied to them in use, the fibers must have a wall thickness (typically of the order of 25–50 micron in the case of microporous fibers for oxygenation) which cannot be considered optimum for the exchange mechanism, which is usually improved or is made easier by smaller wall thicknesses.

Considerations generally similar to those given above also apply to the other exchange structures mentioned initially, for example, for blood purification equipment (operating on various principles such as dialysis, haemofiltration, haemodiafiltration etc.) and/or heat exchangers.

OBJECTS AND SUMMARY OF THE INVENTION

The object of the invention is therefore to provide an exchange structure which, whilst in its essential parts resembles a conventional hollow fiber exchange structure, overcomes its disadvantages, particularly those discussed above, in a radical manner.

According to the present invention, this object is achieved by an exchange structure having the characteristics specifically set out in the following claims.

BRIEF DESCRIPTION OF THE DRAWINGS

The invention will now be described, purely by way of non-limitive example, with reference to the appended drawings, in which:

FIGS. 5 and 6 illustrate two further possible embodiments of a portion of an exchange structure according to the invention; and FIG. 7 is a cross-section common to both the embodiments of FIGS. 5 and 6.

DETAILED DESCRIPTION OF THE INVENTION

Figure 1:
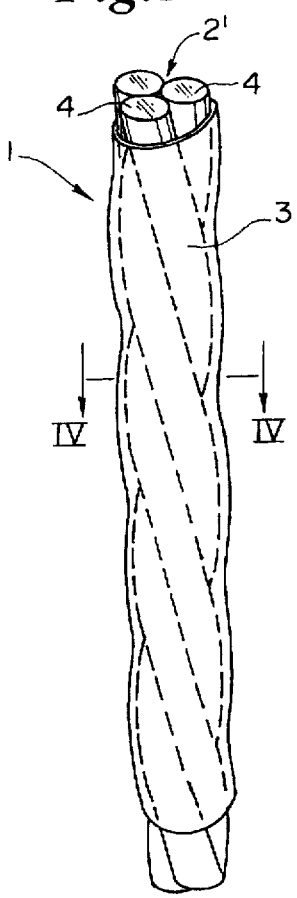
FIG. 1 is a perspective view of a portion of an exchange structure formed according to a first possible embodiment of the invention.
Figure 3:
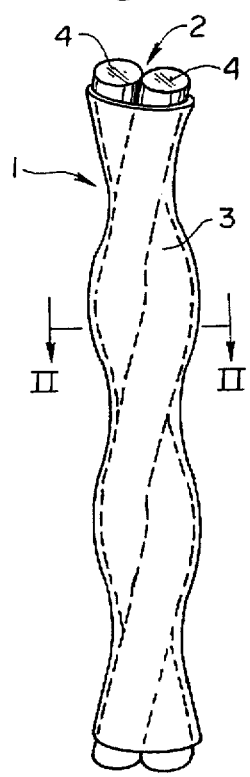
FIG. 3 shows a portion of an exchange structure according to another possible embodiment of the invention.
Figure 2:
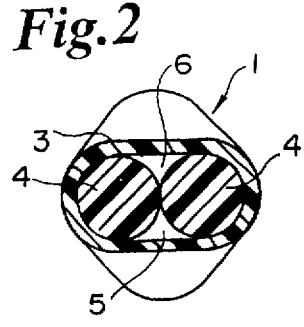
FIG. 2 is a cross-section of the structure of FIG. 1.
Figure 4:
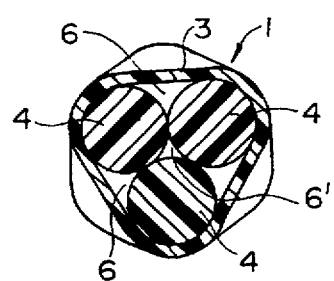
FIG. 4 is a cross-section of the exchange structure of FIG. 3.

As already mentioned above, the exchange structure according to the invention is, to a certain extent, like a fiber structure in the sense that it lends itself to being made in the form of an elongate filamentary body of indefinite length of which FIGS. 1, 3, 5 and 6 show any portion whilst FIGS. 2, 4 and 7 show a section taken on any diametrical plane (the longitudinal position in which this section is taken varies only the relative orientation of the elements considered).

An exchange structure according to the invention, generally indicated 1, comprises essentially two elements, both of indefinite length and therefore capable of being cut to any desired length or wound in any manner entirely similar to those utilized for fibers, that is to say:

a core 2, 2', 2", 2"', which defines the general longitudinal development of the exchange structure 1, and a sheath or covering 3 of generally tubular form (although this configuration is not essential in itself which surrounds the core, 2, 2', 2", 2"', more or less loosely, for example being fitted over the core itself.

In this connection it should be stated that even though explicit reference will be made in the following description to an embodiment in which the core and the sheath are physically separate from one another, being constituted by two separate bodies, the invention also lends itself to being made with arrangements in which the core and the sheath are at least marginally connected together, for example because they are made simultaneously or almost simultaneously, for example by an extrusion, co-extrusion or like operation.

Whatever specific constructional arrangement is adopted, the sheath 3 defines an exchange surface between at least one first medium, which can flow within the space between the internal surfaces of the sheath 3 and the outer surface of the core 2, 2', 2", 2"', and at least one second medium which, in use, flows over the outer surface of the sheath 3 in a mechanism generally similar to that which regulates the functioning of hollow fiber or tune exchange structures.

In the embodiment of FIGS. 1 and 2, the core 2 is formed by two filamentary or fiber elements (here exemplified in the form of solid fibers) preferably wound, at least locally, in a generally helical configuration.

A substantially similar arrangement is adopted for the core 2' of the embodiment of FIGS. 3 and 4 in which there are three filamentary elements 4 (here also shown in the form of solid fibers), preferably coupled in a generally stranded arrangement, also with a generally helical configuration in this case.

In the embodiment of FIGS. 5 and 6, the core is constituted by a profiled body 2" or 2"' with a lobed cross-section, for example with four substantially identical lobes equiangularly spaced at 90° about the longitudinal axis of the core.

The difference between the embodiment of FIG. 5 and the embodiment of FIG. 6 lies in the fact that, whilst the core 2" of FIG. 5 has a generally rectilinear form, the core 2"' of FIG. 6 is, so to say, twisted along its axis such that the lobes 5 are in a generally helical configuration.

With regard to the embodiment illustrated in FIGS. 1, 3 and 6 it should be said that, in these drawings, the helical configuration of the core 2, 2', 2", 2"' has been exaggerated) in order to illustrate the principal clearly (compared with the real situations currently considered preferable.

A characteristic common to all the embodiments illustrated is the fact that the sheath 3 surrounds the core 2, 2", 2"' in such a way as to leave spaces 6 between the core and the inner face of the sheath 3. These spaces define longitudinal flow channels within the exchange structure 1 for one of the media which is involved in the exchange process (of mass or heat) in use of the structure. For example, in the case of a blood oxygenator device, in a haemofilter or a haemodialiser, the spaces 6 define the flow channels for the oxygen, the blood filtrate or the dialysis solution, whilst the blood which is oxygenated or purified flows over the exterior of the sheath 3.

In embodiments such as those of FIGS. 1 to 4, the spaces 6 have a cross-section which is generally V-shaped with rounded sides (defined by the outer surfaces of the fibers 4). To these is added, in the arrangements of FIGS. 3 and 4, a central channel or space 6' of approximately triangular shape. Not being exposed to the sheath 3 and therefore not being usable in the exchange mechanism, this central space 6' can be closed or utilized for other purposes (for example for the passage of guide wire).

It goes without saying that the arrangement described in FIGS. 1 to 4 can readily be extrapolated to the production of further variants of the invention (not illustrated here) in which the core is formed by a strand or braid or four or more filamentary or fiber elements 4.

The provision of a plurality of fibers 4 in a generally helical arrangement enables the outer surface of the sheath 3 also to have generally helically-ribbed shape if fitted tightly, or even slightly loosely around the core 2 or 2'. This particular conformation is advantageous in all those situation in which it is useful to have a degree of turbulence in the medium which flows over the outer surface of the exchange structure in order to achieve effective exchange: for example, in the cases cited above, blood which is to be oxygenated or purified. Similar, substantial turbulence, or at least non-stagnation, of the medium which flows within the exchange structure 1 is promoted by the generally rough form of the channels 6.

The above also applies essentially to the embodiments shown in FIGS. 5 to 7, especially for the embodiment of FIG. 6 in which the core 2"' has a generally helical form.

The variants of FIGS. 5 to 7 have the further advantage that the profiles of the connector surfaces, indicted 6a, interconnecting the lobes 5 can be modified selectively. The surfaces 6a, together with the inner surfaces of the portions of the sheath 3 facing them define the cross-sectional profiles of the spaces or channels 6.

Thus, for example, whilst the drawing of FIG. 7 shows surfaces 6a of generally arcuate shape, these surfaces could have an L or V shape or a polygonal or more complex shape. All this within the recognized preference for shapes in those regions of the lobes 5 intended to come into contact with the sheath which are generally rounded in order to support it: corners which are too sharp would in fact induce wear and possibly rupture of the sheath 3 itself.

It will likewise be appreciated that, in all the embodiments illustrated, it is possible to make the channels 6 of such a shape that, in those regions in which the lobes 5 lie close to the sheath 3, corner regions with extremely small radii are formed. All this is for the purpose of causing, when liquids are present or flowing in the channels 6, capillary phenomena to occur which prevent the formation of gas-liquid fragmentation with the exchanger structure, according to the teachings provided in EP-A-O 521 430.

As regards the choice of constituent materials the structure according to the invention is extremely flexible and can be varied according to specific fields of application.

For example, for the production of mass-exchange structures (oxygenators, dialysers, structures for reverse osmosis, etc.), for the sheath 3 it is possible to use all materials conventionally utilized for the production of exchange membranes or fibers, for example, polymers, polyethylene, polypropylene, polyurethane, polysulphone, silicone, cellulose materials, etc., up to the use of metals in the case of heat-exchange structures, for example metals having a high thermal conductivity (copper, aluminum, steel, etc.)

There is also the possibility, as far as the wall thickness of the sheath 3 is concerned, of using extremely small values, for example, of the order of a few microns, which is optimum for the majority of the applications indicated above, and of making use of unified technologies (for example extrusion, spinning, co-extrusion, etc.) which do not impose particular overriding limitations as regards the dimensions of the structure. These can therefore be shown according to the specific requirements of use, for example as far as the overall section of the channels 6 is concerned. By way of example, structures of the type illustrated in the appended drawings can be made with diameters of the order of 150–400 microns, from which it will easily be understood how, in the drawings, and in particular in the sections of FIGS. 2, 4, and 7, the thickness of the sheath 3, which is a thin-walled body, is shown with dimensions which are greatly enlarged with respect to the real relative dimensions for reasons of clarity of illustration.

The above is also true in essence as regards the production of the cores 2, 2', 2", 2"'. Here, too, the choice of materials in just as wide, it being possible to range from very diverse types of polymer to metals (above all when it is desired to give the structure a certain longitudinal rigidity or strength, for example for the production of devices for catheterization). All this can be achieved by the manufacturer with the use of known manufacturing techniques, such as, typically, extrusion, co-extrusion of the sheath on the core, or fitting of heat-shrinkable sheaths and/or (in the case of structures such as those illustrated in FIGS. 1 and 3) spinning and winding techniques. As already mentioned, the sheath and the core may then consist equally well of two separate bodies or parts of a single body. This is regardless of whether they are made from the same material or are formed from different materials.

Naturally, the principle of the invention remaining the same, the details of construction and the embodiments can be varied widely with respect to those described and illustrated, without thereby departing from the ambit of the present invention.

What is claimed is:

1. An exchange structure capable of forming an exchange relationship between at least two media, said structure comprising:

(a) a generally elongate, filamentary supporting core, and (b) a non-self-supporting, substantially tubular sheath having an inner surface and an outer surface, the sheath surrounding said core so as to define, between the inner surface of the sheath and the core, at least one passage for one of said media, wherein the generally elongate supporting core contacts and supports the non-self-supporting sheath to define, at least in part, the surface geometry of the outer surface of the sheath.

2. An exchange structure as claimed in claim 1, wherein said sheath is a thin-walled body with a wall thickness of less than 25 microns.

3. An exchange structure as claimed in claim 1, wherein said core comprises a plurality of filamentary elements.

4. An exchange structure as claimed in claim 3, wherein said filamentary elements are disposed in an arrangement in which they wrap around each other such as to give said sheath a ribbed external form.

5. An exchange structure as claimed in claim 3 wherein said filamentary elements are wound in a substantially helical arrangement.

6. An exchange structure as claimed in claim 1, wherein said core comprises a profiled body comprising lobes.

7. An exchange structure as claimed in claim 6, wherein said core includes a plurality of equiangularly spaced lobes.

8. An exchange structure as claimed in claim 6, wherein said profiled body has a twisted form such that said lobes extend in a substantially helical form.

9. An exchange structure as claimed in claim 1, wherein said core has regions which contact with said sheath, said regions being substantially rounded in shape.

10. An exchange structure as claimed in claim 1, wherein said core has regions in which said profile of said core in each region defines a passage for one of said media, in said regions said core has a form such as to define corner zones of said passage with radii of curvature such as to induce capillary phenomena in fluid which flows through these regions.

11. An exchange structure as claimed in claim 1, wherein said core and said sheath are made from different materials.

12. An exchange structure as claimed in claim 1, wherein said core and said sheath are made from substantially the same materials.

13. An exchange structure as claimed in claim 1, wherein said core and said sheath are separate bodies.

14. An exchange structure as claimed in claimed 1, wherein said core and said sheath are parts of a single body.

15. An exchange structure as claimed in claim 1, wherein the overall shape of the outer surface of the sheath is determined by the shape of the core.

* * * * *